US009005908B2

(12) United States Patent
Stevenson et al.

(10) Patent No.: US 9,005,908 B2
(45) Date of Patent: Apr. 14, 2015

(54) MYCOBACTERIAL INFECTIONS

(75) Inventors: Karen Stevenson, Edinburgh (GB); Valerie Margaret Hughes, Edinburgh (GB)

(73) Assignee: Moredun Research Institute (GB)

( * ) Notice: Subject to any disclaimer, the term of this patent is extended or adjusted under 35 U.S.C. 154(b) by 975 days.

(21) Appl. No.: 12/994,876

(22) PCT Filed: May 29, 2009

(86) PCT No.: PCT/GB2009/001364
§ 371 (c)(1),
(2), (4) Date: Feb. 15, 2011

(87) PCT Pub. No.: WO2009/144478
PCT Pub. Date: Dec. 3, 2009

(65) Prior Publication Data
US 2011/0135578 A1    Jun. 9, 2011

(30) Foreign Application Priority Data

May 29, 2008    (GB) ................................. 0809761.0

(51) Int. Cl.
G01N 33/00      (2006.01)
A61K 39/04      (2006.01)
A61K 49/00      (2006.01)
G01N 33/569     (2006.01)

(52) U.S. Cl.
CPC ................................. *G01N 33/5695* (2013.01)

(58) Field of Classification Search
USPC .................. 424/9.1, 9.2, 184.1, 185.1, 234.1, 424/248.1; 435/4, 7.1, 7.2, 7.24; 530/350, 530/300
See application file for complete search history.

(56) References Cited

U.S. PATENT DOCUMENTS

2007/0042383 A1*  2/2007  Kapur et al. ..................... 435/6
2008/0038758 A1    2/2008  Momotani et al.

OTHER PUBLICATIONS

Jungersen, G., et al. Clinical and Diagnostic Laboratory Immunology, vol. 9, No. 2, pp. 453-460, Mar. 2002.*
International Search Report Corresponding to International Application No. PCT/GB2009/001364; Date of Mailing: Mar. 10, 2010; 6 pages.
Jungersen G. et al., "Interpretation of the Gamma Interferon Test for Diagnosis of Subclinical Paratuberculosis in Cattle", *Clinical and Diagnostic Laboratory Immunology*, vol. 9, No. 2, Mar. 2002, p. 453-460.
Paustian M. et al., "Characterization of Novel Coding Sequences Specific to Mycobacterium avium subsp. Paratuberculosis: Implication for Diagnosis of Johne's Disease", vol. 42, No. 6, *Journal of Clinical Microbiology*, p. 2675-2681.
Bannantine John P. et al., "Identification of Diagnostic Proteins in Mycobacterium avium subspecies paratuberculosis by a Whole Genome Analysis Approach", *Methods in Molecular Biology*, vol. 345, Jan. 2006, p. 185-196.
Li Lingling et al., "The complete genome sequence of Mycobacterium avium subspecies paratuberculosis", *PNAS*, vol. 102, No. 35, Aug. 30, 2005, p. 12344-12349.
Shin Sung Jae, "In Vitro Cellular Immune Responses to Recombinant Antigens of Mycobacterium avium subsp. paratuberculosis", *Infection and Immunity*, vol. 73, No. 8, Aug. 1, 2005, p. 5074-5085.
Hughes Valerie et al., "Immunogenicity of Proteome-Determined Mycobacterium avium subsp. paratuberculosis-Specific Proteins in Sheep with Paratuberculosis", *Clinical and Vaccine Immunology*, vol. 15, No. 12, Dec. 2008, p. 1824-1833.
Anonymous: "Hypothetical protein MAP0268c [Mycobacterium avium subsp. paratubercul—Protein—NCBI", Dec. 3, 2007, XP55103240, Retrieved from the Internet: URL:http://www.ncbi.nlm.nih.gov/protein/41406366?sat=12&satkey=5460401 [retrieved on Feb. 19, 2014].
Anonymous: "1-(5-phosphoribosyl)-5-[(5-phosphoribosylamino) methylideneamino] imida-Protein—NCBI", Dec. 3, 2007, XP55103239, Retrieved from the Internet: URL:http://www.ncbi.nlm.nih.gov/protein/41407395?sat=12&satkey=5460401 [retrieved on Feb. 19, 2004].
Anonymous: "Ornithine carbamoyltransferase [Mycobacterium avium subsp. paratubercu-Protein—NCBI", Dec. 3, 2012, XP55103242. Retrieved from the Internet: URL:http://www.ncbi.nlm.nih.gov/protein/41407463?sat=12&satkey=5460401 [retrieved on Feb. 19, 2014].
Anonymous: "FadE3_2 [Mycobacterium avium subsp. paratuberculosis K-10]—Protein-NCBI", Dec. 3, 2007, XP55103243, Retrieved from the Internet: URL:http://www.ncbi.nlm.nih.gov/protein/41409749?sat=12&satkey=5460401 [retrieved on Feb. 19, 2014].
Examination Report Corresponding to British Application No. GB 09754123.9 issued Feb. 27, 2014.

* cited by examiner

*Primary Examiner* — Rodney P Swartz
(74) *Attorney, Agent, or Firm* — Myers Bigel Sibley & Sajovec, P.A.

(57) ABSTRACT

The present invention relates to Mycobacterial infections and provides a method of diagnosing infections of *Mycobacterium avium* subsp. *paratuberculosis* (Map), the causative agent of Johne's disease. In addition, the invention also provides as kits for use in the diagnosis of Map infections and vaccines/immunogenic compositions.

10 Claims, 5 Drawing Sheets

```
  1 mtqpdtdwda ayrqaapppw sigrpqpele rlidegkfrs dvldsgcgha alslrlaalg
 61 htvvgldasa taiaeataaa aaqglttatf aradvtdfad yppgsegrfa tivdsglfha
121 lppqrrqdyl rsifraaapg aalyilafaa galapahpdr pgpqgftete lreavsvlwh
181 iddlhaarvy gnddsagapd splahlehdg eghfmapgfl vsahkpd
```

FIGURE 3

```
  1 mlillpavdv vdgravrlvq gkagseteyg saldaalgwq rdgaewihlv dldaafgrgs
 61 nrellaevvg kldvrvelsg girdddslaa alatgcarvn lgtaalenpq wcaraigehg
121 dkvavgldvq iidgqhrlrg rgwetdggdl wevlerlerq gcsryvvtdv tkdgtlggpn
181 ldllgavadr tdapviasgg vsslddlrai atltgrgveg aivgkalyag rftlpqalaa
241 vae
```

FIGURE 4

```
  1 mtprhflrdd dlspaeqaev lalaaelkkd pfsarplegp rgvavlfdkn strtrfsfcv
 61 giaqlgghav vvdarstqlg rdetledtar vlsryveaiv wrtfeqqrle amagaatvpv
121 inalsdefhp cqmladlqai aehkgslsgl rmcylgdgan nmahslmlgg vtagihvtia
181 apdgftpape fvaaarrrae stgatvtltt daraaargvd vlvtdtwtsm gqeddgldrr
241 tpfwpyqlna dlvsladpea ivlhclpahr geeitdevmd gpssvvwdea enrlhaqkal
301 ltwllerqs
```

FIGURE 5

```
  1 mgansrvfaq qvdvrresvr waqvndeedm lvatvrafid revkptvrev ehadaypcaw
 61 ieqmkrigiy glavpeeygg spvsmpcyvr vteqlargwm slagamgght vvaklltlfg
121 tedqkraylp rmasgeirat maltepgggs dlqnmsttal pdpdsdglvv ngaktwisna
181 rrsgliallc ktdpkatprh kgisillveh gpgltvsrdl pklgykgves celsfgnfra
241 patavlggva gqgfsqmmkg letgriqvaa ralgvataal edalayaqqr esfgqpiwqh
301 qsvgnyladm atkltaarql tryaaeryds gercdmeagm aklfasevam eialnavrih
361 ggygysqeyd veryfrdapl mivgegtnei qrnviarqlv trggi
```

FIGURE 6

SEQUENCE LISTING

```
<160> NUMBER OF SEQ ID NOS: 4

<210> SEQ ID NO 1
<211> LENGTH: 227
<212> TYPE: PRT
<213> ORGANISM: Mycobacterium avium subsp. paratuberculosis K-10

<400> SEQUENCE: 1
```

```
Met Thr Gln Pro Asp Thr Asp Trp Asp Ala Ala Tyr Arg Gln Ala Ala
1               5                   10                  15

Pro Pro Pro Trp Ser Ile Gly Arg Pro Gln Pro Glu Leu Glu Arg Leu
            20                  25                  30

Ile Asp Glu Gly Lys Phe Arg Ser Asp Val Leu Asp Ser Gly Cys Gly
            35                  40                  45

His Ala Ala Leu Ser Leu Arg Leu Ala Ala Leu Gly His Thr Val Val
        50                  55                  60

Gly Leu Asp Ala Ser Ala Thr Ala Ile Ala Glu Ala Thr Ala Ala Ala
65                  70                  75                  80

Ala Ala Gln Gly Leu Thr Thr Ala Thr Phe Ala Arg Ala Asp Val Thr
                85                  90                  95

Asp Phe Ala Asp Tyr Pro Pro Gly Ser Glu Gly Arg Phe Ala Thr Ile
            100                 105                 110

Val Asp Ser Gly Leu Phe His Ala Leu Pro Pro Gln Arg Arg Gln Asp
        115                 120                 125

Tyr Leu Arg Ser Ile Phe Arg Ala Ala Ala Pro Gly Ala Ala Leu Tyr
        130                 135                 140

Ile Leu Ala Phe Ala Ala Gly Ala Leu Ala Pro Ala His Pro Asp Arg
145                 150                 155                 160

Pro Gly Pro Gln Gly Phe Thr Glu Thr Glu Leu Arg Glu Ala Val Ser
                165                 170                 175

Val Leu Trp His Ile Asp Asp Leu His Ala Ala Arg Val Tyr Gly Asn
            180                 185                 190

Asp Asp Ser Ala Gly Ala Pro Asp Ser Pro Leu Ala His Leu Glu His
        195                 200                 205

Asp Gly Glu Gly His Phe Met Ala Pro Gly Phe Leu Val Ser Ala His
        210                 215                 220

Lys Pro Asp
225

<210> SEQ ID NO 2
<211> LENGTH: 243
<212> TYPE: PRT
<213> ORGANISM: Mycobacterium avium subsp. paratuberculosis K-10

<400> SEQUENCE: 2

Met Leu Ile Leu Leu Pro Ala Val Asp Val Asp Gly Arg Ala Val
1               5                   10                  15

Arg Leu Val Gln Gly Lys Ala Gly Ser Glu Thr Glu Tyr Gly Ser Ala
            20                  25                  30

Leu Asp Ala Ala Leu Gly Trp Gln Arg Asp Gly Ala Glu Trp Ile His
            35                  40                  45

Leu Val Asp Leu Asp Ala Ala Phe Gly Arg Gly Ser Asn Arg Glu Leu
        50                  55                  60

Leu Ala Glu Val Val Gly Lys Leu Asp Val Arg Val Glu Leu Ser Gly
65                  70                  75                  80

Gly Ile Arg Asp Asp Asp Ser Leu Ala Ala Ala Leu Ala Thr Gly Cys
                85                  90                  95

Ala Arg Val Asn Leu Gly Thr Ala Ala Leu Glu Asn Pro Gln Trp Cys
            100                 105                 110

Ala Arg Ala Ile Gly Glu His Gly Asp Lys Val Ala Val Gly Leu Asp
        115                 120                 125

Val Gln Ile Ile Asp Gly Gln His Arg Leu Arg Gly Arg Gly Trp Glu
        130                 135                 140
```

```
Thr Asp Gly Gly Asp Leu Trp Glu Val Leu Glu Arg Leu Glu Arg Gln
145                 150                 155                 160

Gly Cys Ser Arg Tyr Val Val Thr Asp Val Thr Lys Asp Gly Thr Leu
                165                 170                 175

Gly Gly Pro Asn Leu Asp Leu Leu Gly Ala Val Ala Asp Arg Thr Asp
            180                 185                 190

Ala Pro Val Ile Ala Ser Gly Gly Val Ser Ser Leu Asp Asp Leu Arg
                195                 200                 205

Ala Ile Ala Thr Leu Thr Gly Arg Gly Val Glu Gly Ala Ile Val Gly
            210                 215                 220

Lys Ala Leu Tyr Ala Gly Arg Phe Thr Leu Pro Gln Ala Leu Ala Ala
225                 230                 235                 240

Val Ala Glu

<210> SEQ ID NO 3
<211> LENGTH: 309
<212> TYPE: PRT
<213> ORGANISM: Mycobacterium avium subsp. paratuberculosis K-10

<400> SEQUENCE: 3

Met Thr Pro Arg His Phe Leu Arg Asp Asp Asp Leu Ser Pro Ala Glu
1               5                   10                  15

Gln Ala Glu Val Leu Ala Leu Ala Ala Glu Leu Lys Lys Asp Pro Phe
                20                  25                  30

Ser Ala Arg Pro Leu Glu Gly Pro Arg Gly Val Ala Val Leu Phe Asp
            35                  40                  45

Lys Asn Ser Thr Arg Thr Arg Phe Ser Phe Glu Val Gly Ile Ala Gln
50                  55                  60

Leu Gly Gly His Ala Val Val Val Asp Ala Arg Ser Thr Gln Leu Gly
65                  70                  75                  80

Arg Asp Glu Thr Leu Glu Asp Thr Ala Arg Val Leu Ser Arg Tyr Val
                85                  90                  95

Glu Ala Ile Val Trp Arg Thr Phe Glu Gln Gln Arg Leu Glu Ala Met
                100                 105                 110

Ala Gly Ala Ala Thr Val Pro Val Ile Asn Ala Leu Ser Asp Glu Phe
            115                 120                 125

His Pro Cys Gln Met Leu Ala Asp Leu Gln Ala Ile Ala Glu His Lys
        130                 135                 140

Gly Ser Leu Ser Gly Leu Arg Met Cys Tyr Leu Gly Asp Gly Ala Asn
145                 150                 155                 160

Asn Met Ala His Ser Leu Met Leu Gly Gly Val Thr Ala Gly Ile His
                165                 170                 175

Val Thr Ile Ala Ala Pro Asp Gly Phe Thr Pro Ala Pro Glu Phe Val
            180                 185                 190

Ala Ala Ala Arg Arg Ala Glu Ser Thr Gly Ala Thr Val Thr Leu
        195                 200                 205

Thr Thr Asp Ala Arg Ala Ala Arg Gly Val Asp Val Leu Val Thr
        210                 215                 220

Asp Thr Trp Thr Ser Met Gly Gln Glu Asp Asp Gly Leu Asp Arg Arg
225                 230                 235                 240

Thr Pro Phe Trp Pro Tyr Gln Leu Asn Ala Asp Leu Val Ser Leu Ala
                245                 250                 255

Asp Pro Glu Ala Ile Val Leu His Cys Leu Pro Ala His Arg Gly Glu
                260                 265                 270
```

```
Glu Ile Thr Asp Glu Val Met Asp Gly Pro Ser Ser Val Val Trp Asp
            275                 280                 285

Glu Ala Glu Asn Arg Leu His Ala Gln Lys Ala Leu Leu Thr Trp Leu
290                 295                 300

Leu Glu Arg Gln Ser
305

<210> SEQ ID NO 4
<211> LENGTH: 405
<212> TYPE: PRT
<213> ORGANISM: Mycobacterium avium subsp. paratuberculosis K-10

<400> SEQUENCE: 4

Met Gly Ala Asn Ser Arg Val Phe Ala Gln Gln Val Asp Val Arg Arg
1               5                   10                  15

Glu Ser Val Arg Trp Ala Gln Val Asn Asp Glu Glu Asp Met Leu Val
            20                  25                  30

Ala Thr Val Arg Ala Phe Ile Asp Arg Glu Val Lys Pro Thr Val Arg
        35                  40                  45

Glu Val Glu His Ala Asp Ala Tyr Pro Glu Ala Trp Ile Glu Gln Met
    50                  55                  60

Lys Arg Ile Gly Ile Tyr Gly Leu Ala Val Pro Glu Glu Tyr Gly Gly
65                  70                  75                  80

Ser Pro Val Ser Met Pro Cys Tyr Val Arg Val Thr Gln Leu Ala
                85                  90                  95

Arg Gly Trp Met Ser Leu Ala Gly Ala Met Gly Gly His Thr Val Val
            100                 105                 110

Ala Lys Leu Leu Thr Leu Phe Gly Thr Glu Asp Gln Lys Arg Ala Tyr
        115                 120                 125

Leu Pro Arg Met Ala Ser Gly Glu Ile Arg Ala Thr Met Ala Leu Thr
    130                 135                 140

Glu Pro Gly Gly Gly Ser Asp Leu Gln Asn Met Ser Thr Thr Ala Leu
145                 150                 155                 160

Pro Asp Pro Asp Ser Asp Gly Leu Val Val Asn Gly Ala Lys Thr Trp
                165                 170                 175

Ile Ser Asn Ala Arg Arg Ser Gly Leu Ile Ala Leu Leu Cys Lys Thr
            180                 185                 190

Asp Pro Lys Ala Thr Pro Arg His Lys Gly Ile Ser Ile Leu Leu Val
        195                 200                 205

Glu His Gly Pro Gly Leu Thr Val Ser Arg Asp Leu Pro Lys Leu Gly
    210                 215                 220

Tyr Lys Gly Val Glu Ser Cys Glu Leu Ser Phe Gly Asn Phe Arg Ala
225                 230                 235                 240

Pro Ala Thr Ala Val Leu Gly Gly Val Ala Gly Gln Gly Phe Ser Gln
                245                 250                 255

Met Met Lys Gly Leu Glu Thr Gly Arg Ile Gln Val Ala Ala Arg Ala
            260                 265                 270

Leu Gly Val Ala Thr Ala Ala Leu Glu Asp Ala Leu Ala Tyr Ala Gln
        275                 280                 285

Gln Arg Glu Ser Phe Gly Gln Pro Ile Trp Gln His Gln Ser Val Gly
    290                 295                 300

Asn Tyr Leu Ala Asp Met Ala Thr Lys Leu Thr Ala Ala Arg Gln Leu
305                 310                 315                 320
```

-continued

```
Thr Arg Tyr Ala Ala Glu Arg Tyr Asp Ser Gly Glu Arg Cys Asp Met
            325                 330                 335

Glu Ala Gly Met Ala Lys Leu Phe Ala Ser Glu Val Ala Met Glu Ile
            340                 345                 350

Ala Leu Asn Ala Val Arg Ile His Gly Gly Tyr Gly Tyr Ser Gln Glu
        355                 360                 365

Tyr Asp Val Glu Arg Tyr Phe Arg Asp Ala Pro Leu Met Ile Val Gly
    370                 375                 380

Glu Gly Thr Asn Glu Ile Gln Arg Asn Val Ile Ala Arg Gln Leu Val
385                 390                 395                 400

Thr Arg Gly Gly Ile
            405
```

MYCOBACTERIAL INFECTIONS

RELATED APPLICATIONS

This application is a 35 U.S.C. §371 national phase entry of PCT Application PCT/GB2009/001364, filed May 29, 2009, and published in English on Dec. 3, 2009, as International Publication No. WO 2009/144478, and which claims the benefit of Great Britain Application No. 0809761.0, filed May 29, 2008, the disclosure of each of which is incorporated herein by reference in its entirety.

STATEMENT REGARDING ELECTRONIC FILING OF A SEQUENCE LISTING

A Sequence Listing in ASCII text format, submitted under 37 C.F.R. §1.821, entitled 9013-107_ST25.txt, 10,848 bytes in size, generated on Jan. 10, 2013 and filed via EFS-Web, is provided in lieu of a paper copy. This Sequence Listing is hereby incorporated herein by reference into the specification for its disclosures.

FIELD OF THE INVENTION

The present invention relates generally to Mycobacterial infections and provides a method of diagnosing infections of *Mycobacterium avium* subspecies *paratuberculosis* (Map), the causative agent of Johne's disease, as well as kits for use in such diagnosis and vaccines.

BACKGROUND TO THE INVENTION

Johne's disease, or paratuberculosis, is a fatal chronic granulomatous enteritis of animals caused by Map. The disease is characterised by severe emaciation, loss of body condition and in some species diarrhea. The disease is mainly spread through the ingestion of faeces from an infected animal. Infected animals can also pass on the infection in colostrum or milk and across the placenta to unborn animals. It is generally believed that young animals are more susceptible to infection than adults. Following infection there is a long incubation period of 2 to 4 years during which time the animal may show no signs of clinical disease and may shed Map intermittently. Such animals are often described as "subclinically infected" and act as "carriers" of the disease. The disease is usually introduced to a farm through the purchase of subclinically infected stock.

Johne's disease occurs worldwide and causes considerable economic losses through decreased productivity, increased wastage of adult animals as well as the cost of control, monitoring and diagnosis. There is also some controversy as to whether Map is involved in the development of Crohn's disease. Contaminated milk would constitute a source of infection and there is a drive towards elimination of Map from the food chain.

The diagnosis of Johne's disease is problematic and there is no single diagnostic test that can detect all stages of the disease. Subclinically infected animals are particularly difficult to diagnose and results of currently available tests may be negative. The most commonly used diagnostic test is the serum Enzyme Linked Immunosorbent Assay (ELISA). This detects circulating antibodies to Map in infected animals. It will detect animals in the later stages of the disease, where clinical symptoms are often present, which are generally those shedding large numbers of Map. It will not, however, detect animals in the early stages of infection, typified as being subclinical where the antibody levels are below the sensitivity threshold of the test. The other most commonly used tests are faecal smears and bacteriological culture. Faecal smears detect the presence of acid-fast bacteria in the faeces and probably only detect a third of the infected animals in a herd/flock. Bacteriological culture is more sensitive and specific but takes 6 weeks or more which is less than desirable. Moreover, low shedders can sometimes be difficult to detect and subclinically infected animals are often missed because they shed intermittently.

PCR-based tests are not used routinely as yet but are available for detecting Map in milk, blood or faeces. Also there are particular problems with the application of PCR tests to milk, blood and faecal samples. There is therefore a requirement for a test that can detect early infection and subclinically infected animals.

It is amongst the objects of the present invention to obviate and/or mitigate at least one of the aforementioned disadvantages.

SUMMARY OF THE INVENTION

The present invention is based on the identification of Map antigens which are capable of causing a cell-mediated immune response.

In the first aspect there is provided a method of detecting a cell-mediated immune response to one or more purified antigens of Map in an animal, the method comprising the step of:

detection of a cell-mediated immune response by measuring the extent of lymphocyte activation and/or proliferation in response to said one or more purified antigens of Map.

For example, the cell-mediated immune response may be measured by detecting a level of cytokine such as interferon gamma (IFN-γ), tumour necrosis factor alpha (TNF-α), transforming growth factor beta (TGF-β), interleukins (IL-2, IL-6, IL-10, IL-12, IL-17) and granulocyte-macrophage colony-stimulating factor (GM-CSF) using antibodies or indirectly from mRNA by RT-PCR or microarray. Proliferation may be assayed by incorporation of labelled precursors of DNA or protein into the lymphocytes undergoing proliferation.

The method may be carried out on a blood sample, or a fraction thereof, isolated from a subject, or may be a skin test, such as a delayed hypersensitivity skin test.

Conveniently the blood sample is a whole blood sample obtained from the animal to be tested. Alternatively purified or semi-purified fractions of whole blood, which comprise lymphocytes and monocytes may be employed. Typical amounts of sample required for testing may be 10 µl to 10 ml. Advantageously, a single blood sample would enable testing of an animal's responsiveness to a wide variety of antigens and therefore diagnosis of other diseases.

It will be appreciated that the sample of blood will generally be incubated with said one or more purified Map antigens, for a period of time (e.g. from 1 min to 96 hours but typically from 4 to 72 hours) so as to allow any cell-mediated response (e.g. IFN-γ production), as a result of said one or more purified Map antigens, to develop. IFN-γ is produced from T cells present in the sample of blood which are stimulated to produce IFN-γ by said one or more purified Map antigens.

Unlike other similar cell-mediated tests which are known for detecting animals which are infected with, for example, *Mycobacterium bovis* and/or *Mycobacterium tuberculosis* using uncharacterised, what are termed "purified protein derivatives" (PPD) or "protoplasmic antigen" (PPA), the present invention is based upon the use of purified antigens which are expected as being specific. Map-specific antigens are defined here as proteins or fragments thereof that are expressed by Map and elicit an immune response in animals infected by Map which is greater than that elicited by animals infected by other closely related subspecies of *Mycobacterium avium* (*Mycobacterium avium* subspecies *avium* (Maa) and *Mycobacterium avium* subspecies *silvaticum*). In this manner, the present methods may be carried out on animals or herds of animals exposed to other mycobacterial infections including environmental mycobacteria such that a clear distinction can be obtained. Thus, the one or more Map-specific antigens of the present invention will generally be chosen so as to be highly specific for Map and/or to display little or no cross-reactivity with other related species such as other subspecies of *Mycobacterium avium*, *Mycobacterium bovis* and/or *Mycobacterium tuberculosis*.

Said one or more purified Map-specific antigens may be identified by way of electrophoretically separating the proteome of a Map isolate and comparing this to a highly related species of *Mycobacterium*, such as Maa, in order to identify proteins which are unique to Map and/or differentially expressed. Typically electrophoretic separation may be conducted using a 2-D gel electrophoresis technique well known in the art (see for example Richard Simpson—Proteins and Proteomics: A Laboratory Manual published by Cold Spring Harbor Laboratory Press U.S. 2002) and the proteome of a Map isolate compared to the proteome of the other subspecies. In this manner uniquely and/or differentially expressed proteins can be identified for further study and used as an antigen in accordance with the present invention.

In this manner, the present inventors have identified over 30 proteins, which may be of use individually and/or in combination in a method of the present invention. Details of the proteins may be found in attached Table 1. Preferably, the method of the present invention uses two or more Map-specific antigens, such as 3, 4, 5, 6 or more antigens. It is to be understood that a purified antigen may be a whole protein, or immunogenic protein fragment. Such immunogenic protein fragments must be capable of causing a cell-mediated immune response. Once a whole protein has been identified as being capable of eliciting an appropriate cell-mediated immune response, it is straightforward to create protein fragments of said protein and identify whether or not suitable fragments, are also capable of eliciting a cell-mediated immune response.

Four particularly preferred Map proteins, of which one or more may be used in the present invention, are identified herein as MAP0268c, MAP1297, MAP1365 and MAP3651c and correspond to proteins having the following NCBI database accession numbers, respectively AAS02585, AAS03614, AAS03682 and AAS06201. The sequences identified in the above accessions are from a Map isolate K-10 (Li et al., 2005) and are shown in FIGS. 3-6. It will be understood that minor differences in protein sequence may be identified from one Map isolate to another and as such the proteins identified herein may not be identical in sequence to the corresponding Map K-10 protein identified in the protein database. However, the skilled addressee would be able to easily ascertain if the proteins correspond to one another. In this regard the Map-specific proteins or immunogenic fragments thereof of the present invention will be at least 95%, 98% or 99% identical to a Map K-10 protein or fragment as shown in FIGS. 3-6.

The present invention extends to a process for the purification of recombinant Map-specific proteins from bacterial or eukaryotic expression systems by the cloning and expression in a host cell such as *Eschericia coli*. (see for example Sambrook: Molecular cloning: A laboratory manual (3$^{rd}$ Ed) Cold Spring Harbour Laboratory Press. 2001).

In a further aspect, the present invention provides use of one or more purified Map-specific proteins or immunogenic fragments thereof in a method of diagnosing Map infection in an animal.

Said Map-specific protein or immunogenic fragment thereof is/are preferably one or more of the proteins identified herein, such as those designated MAP0268c, MAP1297, MAP1365 and MAP3651c or immunogenic fragment thereof; or a protein or protein fragment displaying substantial identity with a protein or fragment thereof as shown in FIGS. 3-6.

There is also provided a kit for carrying out a method of diagnosing a Map infection, the kit comprising one or more purified Map-specific proteins or immunogenic fragments thereof capable of eliciting a cell-mediated immune response. Such a kit may further comprise other reagents for use in the method of diagnosis, such as an anti-IFN-γ antibody.

This invention also provides vaccines and immunogenic formulations which may be used to protect animals, particularly cattle, from MAP infection. In one aspect, the present invention provides one or more of the MAP antigens described herein (or fragments, analogues or derivatives thereof) for raising an immune response in an animal.

In a yet further aspect, the present invention provides an immunogenic formulation comprising one or more of the MAP antigens described herein (or fragments, analogues or derivatives thereof).

In one embodiment, the vaccines and immunogenic formulations described herein comprise combinations of two more of the MAP antigens (or fragments, analogues or derivatives thereof) described herein.

One of skill in this field will appreciate that immunogenic formulations of the type suitable for use as a vaccine may be formulated for oral or topical administration. Additionally or alternatively, the immunogenic formulations may be formulated for direct injection, preferably intraperitoneal or intramuscular injection.

The present invention also provides a method of vaccinating or immunising an animal against a MAP infection, said method comprising the step of administering one or more of the MAP antigens (or fragments, analogues or derivatives thereof) described herein.

In one embodiment, the present invention may extend to vaccines, immunogenic compositions and methods for use in protecting animals against developing diseases caused or contributed to, by Map. Such diseases may include, for example, Johne's disease. In other embodiments, the vaccines and immunogenic formulations provided by this invention may not protect against Map infection but may reduce the progression of disease, the level of Map colonisation in a host organism and/or the severity of the symptoms of a disease caused or contributed to by Map.

DETAILED DESCRIPTION

The present invention will now be described by way of example and with reference to the Figures which show:

FIG. 3 shows the protein sequence of a Map K-10 isolate protein (AAS02585), corresponding to MAP0268c of the present invention (SEQ ID NO:1);

FIG. 4 shows the protein sequence of a Map K-10 isolate protein (AAS03614), corresponding to MAP1297 of the present invention (SEQ ID NO:2);

FIG. 5 shows the protein sequence of a Map K-10 isolate protein (AAS03682), corresponding to MAP1365 of the present invention (SEQ ID NO:3); and FIG. 6 shows the protein sequence of a Map K-10 isolate protein (AAS06201), corresponding to MAP3651c of the present invention (SEQ ID NO:4).

Figure 7:
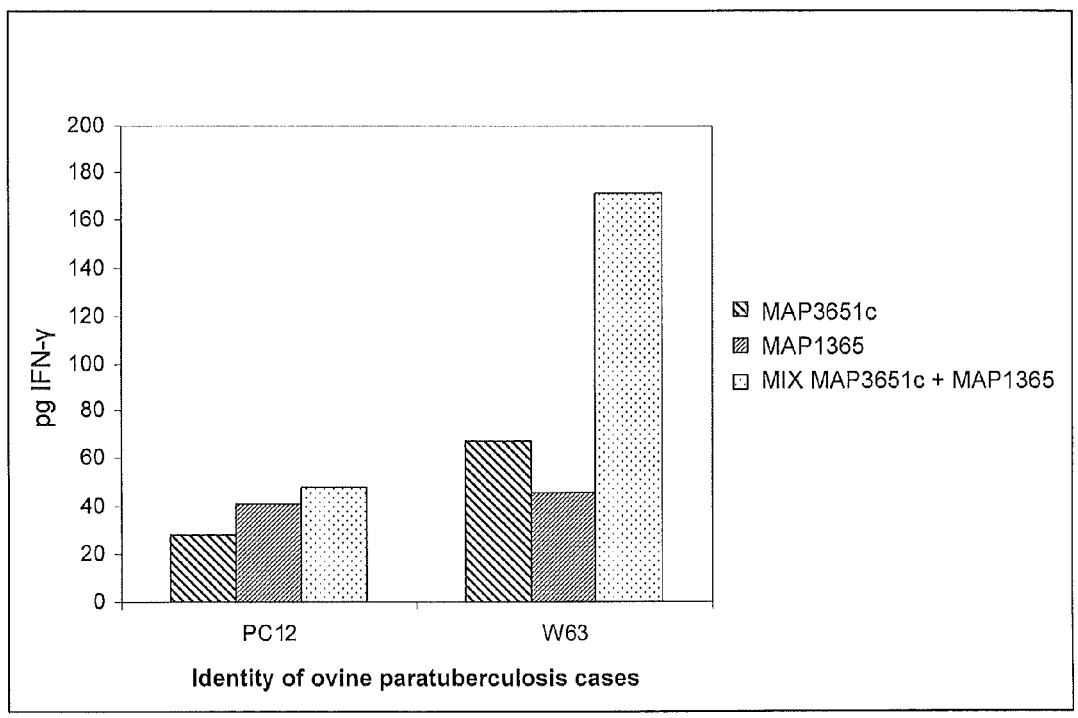

FIG. 7 shows the enhanced stimulation with cocktails of Map-specific antigens. Blood was stimulated with 113.8 μg/ml of recombinant MAP3651c, 125 μg/ml of 1365 and a mix of 113.8 μg/ml of MAP3651c plus 65 μg/ml of MAP1365. Bovigam IFN-γ ELISA responses to antigens expressed as picogrammes of IFN-γ produced. PC12 and W63 were subclinical ovine paratuberculosis cases resulting from natural Map infection.

Figure 8:
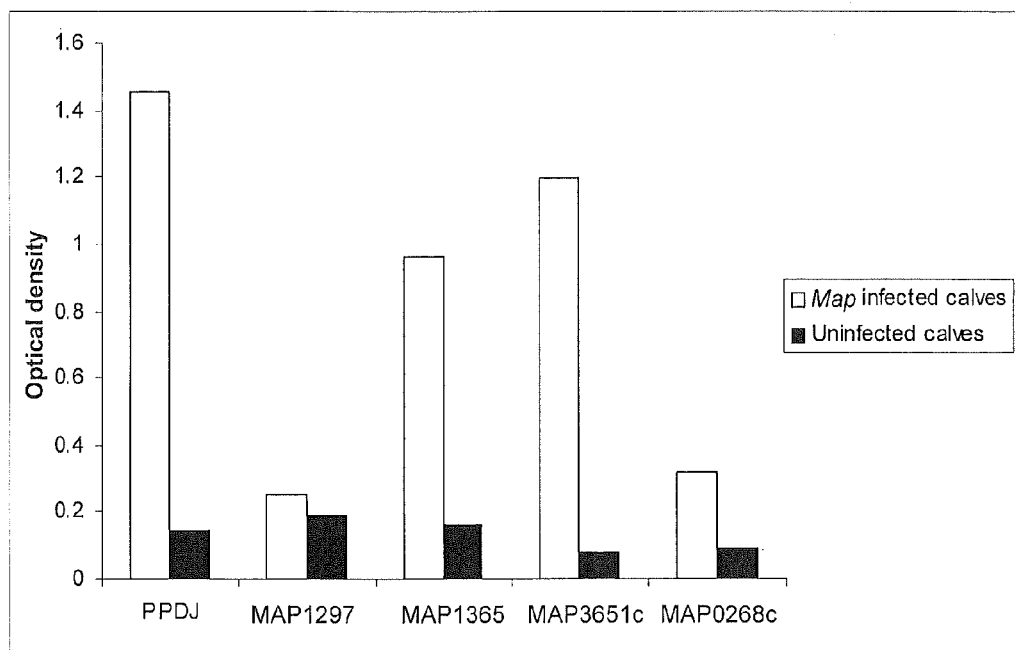

FIG. 8 shows Bovigam IFN-γ ELISA responses of Map experimentally infected and uninfected calves to antigens (final concentration 4 μg/ml) expressed as optical density (OD). Mean OD calculated for duplicate samples for each group of calves. Note Map-infected calves were inoculated with three different concentrations of Map as given in text.

Figure 9:
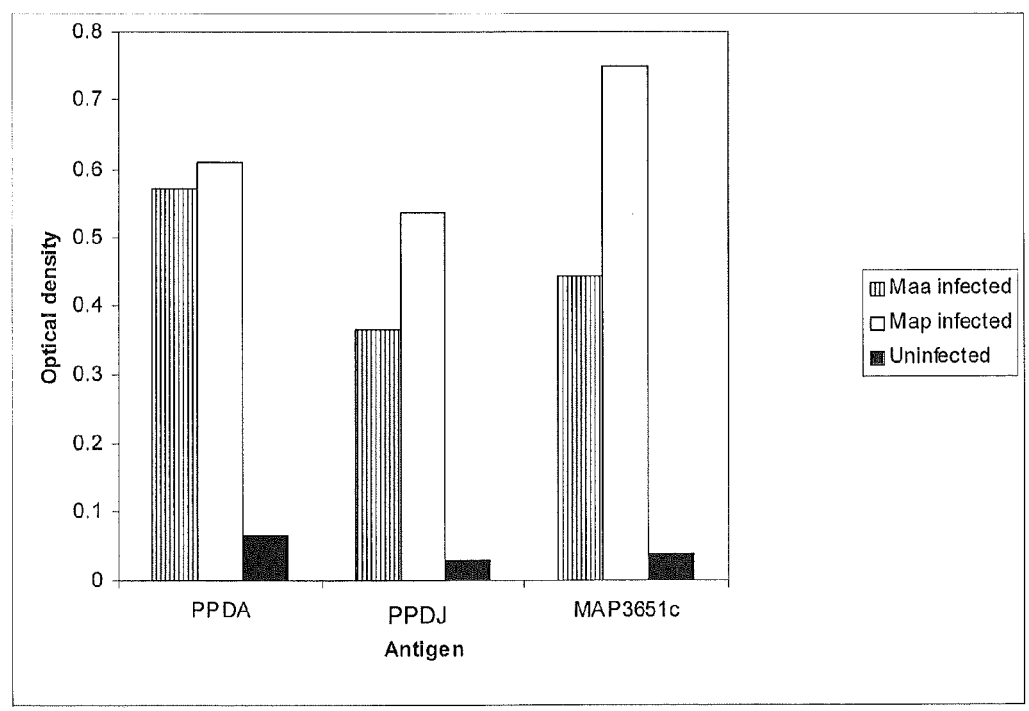

FIG. 9 shows the specificity of the cell-mediated immune response of Map-infected calves compared with Maa-infected calves to recombinant MAP3651c. Blood was stimulated with 7.3 μg/ml of recombinant MAP3651c, 4 μg/ml PPDA and 2 μg/ml PPDJ. Concentrations of the antigens have not been optimised for the diagnostic assay. Bovigam IFN-γ ELISA responses to antigens expressed as optical density (OD). Mean OD calculated for duplicate samples for each group of calves; Maa-infected n=6, Map-infected n=2.

EXAMPLES SECTION

The methods and Table 1 which follow correspond to information described in a paper submitted by the present inventors to Clinical and Vaccine Immunology (Hughes, V., Bannantine, J. P, Denham, S. et al 2008. Clin. Vaccine Immunol. 15: 1824-1833), the copyright of which is acknowledged.

Source and Growth of Microbial Strains

Map strain (JD88/107) was originally isolated from a deer with clinical paratuberculosis. It is mycobactin dependent and IS900 positive. Maa strain (JD88/118) was originally isolated from a deer and is IS901 positive.

Routine propagation and maintenance of mycobacteria were carried out as described in Hughes et al. (2007) For propagating mycobacteria for proteome analysis, starter cultures were initiated by inoculating a loopful of mycobacteria (from a 7H11 slope with confluent growth) into a 10 ml volume of Middlebrook 7H9 medium supplemented with 10% (v/v) Middlebrook OADC 0.1% (w/v) Tween-80, 2 μg ml$^{-1}$ Mycobactin J and 2.5% (v/v) glycerol. The cultures, contained in 50 ml flasks, were stirred continuously using magnetic stirrer bars, on a multiple position low heat transmission magnetic stirrer. After 48 h incubation, 3 ml of the starter culture was transferred to 300 ml of pre-warmed medium in liter flasks. The cultures were incubated at 37° C. with continuous stirring and growth monitored by optical density (OD) at 600 nm as described by Hughes et al. (2007).

When cultures were deemed to have reached either exponential or stationary phase and achieved an OD of at least one, they were assessed for contamination by Ziehl Nielsen staining and light microscopy.

50 ml aliquots were removed asceptically, cooled on ice and then centrifuged (4000 g, 30 min, 4° C.). The supernatant was decanted and the cell pellet carefully resuspended in 25 ml of ice-cold PBS. The cell suspension was then centrifuged again (4000 g, 30 min, 4° C.), supernatant removed and the pellet stored at −20° C. Cell pellets were stored for no longer than one week before further processing for proteomic analyses.

Protein Preparation for 2-D Gel Electrophoresis

This was essentially as described previously (Hughes et al 2007). Briefly, cells (0.2-0.3 g wet-weight) were suspended in 2% (w/v) SDS, 0.04 M Tris, 0.06 M DTT. The suspension was layered onto washed 0.1 mm zirconium/silica beads (Biospec Products, Bartlesville, Ok, USA). The mixture was lysed six times using a Fastprep 120 (Qbiogene, Cambridge, UK) at 6.5 beats/sec with 1 min cooling on ice between each round. The resulting suspension was centrifuged (500 g, 30 s, room temperature) to reduce frothing. The supernatant was pipetted into microcentrifuge tubes and heated to 100° C. for 5 min. It was then rapidly cooled and centrifuged (21000 g, 20 min, at room temperature). The protein extract was stored at −70° C. until required.

Protein clean-up was performed as described in the protocol accompanying the PlusOne 2-D Clean-Up Kit (Amersham Bioscience, Bucks, UK).

The pellet obtained after the clean-up procedure was prepared for isoelectric focussing (IEF) essentially as described by Hughes et al. 2007. Soluble protein extracts were used immediately or stored at −70° C.

The concentration of protein extracts was determined using the PlusOne Quant Kit (Amersham Biosciences, Bucks, UK) and was performed essentially as described in the protocol accompanying the product. The results of the assay were routinely confirmed by visual assessment of the protein loaded onto a 1-D SDS polyacrylamide gel.

Proteomic Analysis

IEF of proteins (150-200 μg for silver stained gels, or 300-500 μg for colloidal coomassie brilliant blue [CBB] stained gels) was performed as described previously (Hughes et al. 2007). Strips were either stored at −70° C. until required or equilibrated prior to electrophoresis in the second dimension.

IEF strips were incubated in SDS equilibration buffer (0.05 M Tris, 6 M urea, 0.065 M DTT, 30% (v/v) glycerol, 2% (w/v) SDS and 0.002% (w/v) bromophenol blue) for 15 mins with gentle shaking followed by a similar incubation in a fresh aliquot of equilibrium buffer containing iodoacetamide (0.135 M). Polyacrylamide gels (26×20 cm 12.5% (w/v), Amersham Biosciences) were electrophoresed using an Ettan Dalt system (Amersham Biosciences), 1 W per gel, overnight, at 15° C. The power was then increased to 2-4 W per gel until the dye-front was within 1 cm of the bottom of the gel.

Gels were stained with either silver using the method described by Morrissey, 1981, with the exception that the glutaraldehyde fix (step 2) was omitted, or colloidal CBB using the method described by Neuhoff et al, 1985.

Scanned Gel images were obtained using a Umax PowerLook III Imagescanner coupled with Imagemaster Labscan v 3.01 software (Amersham Bioscience, Bucks, UK). Image analyses and gel comparisons were subsequently performed using Imagemaster Progenesis software (Nonlinear Dynamics. Newcastle-on-Tyne, UK).

For each individual spot, the differences in median spot volume between Map and Maa were assessed using a Mann-Whitney test. Because a large number of tests were carried out it was necessary to adjust the P-value from each test to allow for this multiple testing. The False Discovery Rate (FDR)

approach of Benjamini and Hochberg, 1995 was used; with an FDR of 5% it would be expected that 5% of the spots identified as differentially expressed would be false positives.
Identification of Proteins and Mass Spectroscopy Proteins of interest were excised from gels with either a 15 or 30 mm 'spot picker' (The Gel Company, San Francisco, Calif., USA) and cut into small pieces approx 1 to 2 mm in diameter, no excess gel from around the spot was taken. Gel pieces were incubated with 0.1 M ammonium bicarbonate, 50% (v/v) ACN for 15 min at room temperature with at least three changes until the stain had been removed. Finally the gel pieces were dehydrated with ACN 100% (v/v) for 10 min. The ACN was removed and the gel pieces were dried using a speed-vac (Thermo Electron Corporation, MA, USA). The gel pieces were rehydrated in 0.01 M DTT, 0.1 M ammonium bicarbonate and incubated at 56° C. for 1 hr followed by treatment with 0.055 M iodoacetamide, 0.1 M ammonium bicarbonate for 30 mins at room temperature in the dark. Gel pieces were washed with 0.1 M ammonium bicarbonate, ACN 50% (v/v) with at least two changes, dehydrated in ACN 100% (v/v) for 10 mins and then dried on the speed vac for 20 min. Proteolytic digestion was carried out using trypsin solution (10 ng/μl 'Promega sequencing grade modified' in 0.025 M ammonium bicarbonate) at 37° C. for at least 16 hr. Protein digest (0.5 μl) was mixed with 0.5 μl of a solution containing 10 mg/ml CHCA, 50% (v/v) ACN, 0.1% (v/v) TFA for analysis by MALDI-TOF on a Voyager-DE Pro mass spectrometer (PerSeptive Biosystems Inc., Framingham, Mass., USA) selecting for a mass range of 600-5000 Da.

Silver stained spots were first de-stained using a commercial kit (SilverQuest, Invitrogen, Paisley, UK) prior to the first dehydration step. All subsequent steps were identical to those used for CBB stained spots as described above.

Data Explorer was used to create the peak list from the raw data with the smoothing function applied, signal to noise correlation factor was set at 0.7 and the data was baseline corrected with the following parameters: peak width 32, flexibility 0.5 and degree 0.1. The peak height at which centroids were calculated was 50% and peaks were de-isotoped. Resolution for mass spectrometry was greater than 10,000 with a mass accuracy of +/−0.01%. A close-external means of calibrating each spectrum, and no means of exclusion of known contaminant ions (such as keratin) were employed.
Bioinformatics The proteome of Map strain K10 (accession numbers NC_002944, AE016958) contains 4350 predicted open reading frames which were used to compile a protein database and this was queried using Mascot 2.0 (Matrix Science Ltd., London, UK) (Perkins et al., 1999). Searches for trypsin cleavage patterns used a fragment ion mass accuracy of 100 ppm, carbamidomethyl modification was selected and up to one missed cleavage site permitted.

Proteins identified using this procedure were characterized using Entrez nr Peptide Sequence data base (National Center For Biotechnology Information [NCBI]) using protein-protein BLAST program. The NCBI Conserved Domain Search service was used to identify domains present in protein query sequences and the Kyoto Encyclopedia of Genes and Genomes was used to identify relevant metabolic pathways.
Cloning and Expression of Map-Specific Sequences Maltose binding protein (MBP) fusions of 30 Map predicted coding sequences were produced in *E. coli* by using the pMAL-c2X vector (New England Biolabs, Beverly, Mass., USA). Primers were designed from the reading frame of each coding sequence and contained an XbaI site in the 5' primer and a HindIII site in the 3' primer for cloning purposes. Amplifications were performed by using AmpliTaq Gold polymerase (Applied Biosystems, CA, USA) and Map genomic DNA as the template under conditions described previously (Bannantine, et al. 2002), The vector and amplification product were digested with XbaI and HindIII. Ligation of these restricted DNA fragments resulted in an in-frame fusion between the malE gene in the vector and the reading frame of interest. Following ligation, the products were transformed into *E. coli* DH5α and selected on LB agar plates containing 100 μg of ampicillin/ml. (Bannantine et a/l. 2004)

Recombinant proteins were prepared essentially as described in the pMAL™ protein fusion and purification system instruction manual (version 5.1, 1/06) with a few minor modifications.

Cultures from which recombinant proteins were extracted where grown in medium containing 50 μg/ml Ampicillin.

Lysis of *E. coli* was carried out in column buffer containing 2% Tween-80 and protease inhibitor cocktail Set III (Merck cat#539134) using a FastPrep FP120 (speed 5.5 for 20 sec, three times with cooling on ice between each round).

MBP fusion protein was prepared from *E. coli* DH5α or TB1 harbouring the parental plasmid pMAL-c2X as described above for Map recombinant proteins and used as a control in all experiments. Purified protein from this control strain consists of an MBP fusion of the LacZ alpha peptide (Bannantine at al. 2004).
Preparation and Stimulation of Ovine Peripheral Blood Lymphocytes 20 ml of blood were collected by venipuncture and placed into tubes containing preservative-free heparin. The blood was centrifuged at 638 g (for 15 min at 15° C.). Samples of plasma were removed and stored at −20° C. until analysis by ELISA. Buffy coat was removed and mixed with 10 ml of Hanks/Hep buffer, (Hanks Balanced Salt Solution, w/o $Ca^{2+}$ or $Mg^{2+}$ with 1% Heparin [Sigma-Aldrich, Poole, England]) and this was then layered over 10 ml of Lymphoprep™ (Axis-Shield, Oslo, Norway) and centrifuged at 1133 g (30 min, 15° C.). The lymphocyte band was aspirated, diluted with 15 ml of Hanks/Hep solution, and centrifuged at 238 g (10 min, 4° C.). The lymphocyte pellet was resuspended in 1 ml lysis buffer (1 part Tris: 9 parts 0.83% Ammonium Chloride, pH 7.2) and incubated on ice for 10 minutes. 9 ml of Hanks/Hep was added and the suspension again centrifuged 238 g (10 min, 4° C.). The cell pellet was resuspended in 1 ml RPMI Complete medium containing RPMI1640 (Gibco, Invitrogen, Paisley, UK), Foetal bovine serum 10% V/V, (Gibco, Invitrogen, Paisley, UK), Glutamine 1 mM (Gibco, Invitrogen, Paisley, UK), 25 mM HEPES (Sigma-Aldrich, Poole, Dorset, UK) 0.08% (V/V) Sodium bicarbonate, 50 μM β-mercaptoethanol (Gibco, Invitrogen, Paisley, UK) and a cocktail of antibiotics (penicillin/streptomycin 100 U/ml (100 μg/ml) gentamycin (100 μg/ml) and the viable cells in this suspension were counted using nigrosin exclusion (20 μl cell suspension mixed with 20 μl 0.1% nigrosin) in a modified Neubauer chamber. The suspension was diluted in RPMI complete to a $2\times10^6$ cells/ml solution. 50 μl of recombinant protein (110 μg/ml in RPMI complete) and 100 μl Lymphocytes ($2\times10^{X6}$ in RPMI complete) were added to microtitre wells and incubated in a humidified box at 37° C. in a humidified atmosphere for 96 h. Microtitre plates were centrifuged at 443 g (5 min, 15° C.). 400 ul of supernatant was removed from each well and stored at 4° C. until ELISA analysis.
Bovine IFN-γ Assay.

The IFN-γ assay was performed on duplicate supernatants from the lymphocytes as described in the manual from BOVI-GAM kit (Prionics A.G., Switzerland). Absorbance readings in ELISA wells were read at 450 nm within 5 min of the reaction being stopped.

Stimulation of Whole Blood with Cocktails of Map-Specific Antigens

Recombinant antigens were prepared as described previously and diluted in sterile PBS. A cocktail of recombinant Map-specific proteins MAP3651c and MAP1365 was prepared by mixing 113.8 µg/ml of MAP3651c plus 65 µg/ml of MAP1365. The cell-mediated immune responses of sheep were measured using the Bovigam IFN-γ ELISA according to the manufacturer's instructions with the following modifications. Fifty microliters of antigen preparation in PBS was mixed with 750 microliters of whole blood in a 24 well sterile culture plate. Blood was cultured within one hour of collection. Approximately 400 microliters of supernatant was collected following a 48 hour incubation period. Incubation with the chromogen was carried out for 15 minutes at 37° C. Blood was stimulated with 113.8 µg/ml of recombinant MAP3651c, 125 µg/ml of MAP1365 and the cocktail of MAP3651c and MAP1365.

Experimental Infection of Calves

Eighteen Holstein male calves were obtained from a herd free from Johne's disease as determined by ELISA testing and faecal culture. The calves were randomly assigned to three groups of six calves. One group was infected at an average age of 16 weeks (14-17) with an IS901 positive strain of Maa, each calf receiving a single dose of $10^9$ organisms. The second group was infected at an average age of 19 weeks (18-21) with Map. Two calves received a single dose of $10^7$, two received $10^8$ and two received $10^9$ organisms. The third group, the uninfected controls received phosphate buffered saline (PBS). The number of organisms was estimated using the wet weight method and the inocula were given orally as a bacterial suspension in PBS. Blood samples were taken for analyses 54, 57 and 48, 51 weeks post infection for Maa and Map infected calves, respectively.

Measurement of Cell-Mediated Responses of Infected Calves

The cell-mediated responses of the infected calves were measured using the Bovigam IFN-γ ELISA (Prionics, Schieren, Switzerland) according to the manufacturer's instructions with the following modifications. The stimulating antigens used were PPDA, PPDJ and recombinant proteins 3651c, 1365, 1297, 0268c at the concentrations given in the figure legends. PPDA was obtained from VLA and dialysed first to remove the phenol. PPDJ was obtained from Douwe Bakker (Central Veterinary Institute of Wageningen University, Lelystad, The Netherlands). Recombinant antigens were prepared as described previously. Twenty five microliters of antigen preparation in PBS was mixed with 200 microliters of whole blood in a 96 well sterile culture plate. Blood was cultured within one hour of collection. Approximately 120 microliters of supernatant was collected following a 24 hour incubation period. For each incubation step in the Bovigam ELISA plates were incubated at 37° C. for one hour. Plates were washed using an automated plate washer six times between steps. Incubation with the chromogen was carried out for ten minutes at 37° C. All antigens were tested in duplicate.

Example 1

Proteomic Identification of Map-Specific Proteins

Map-specific antigens were identified by comparison of the proteomes of Map and IS901+ Maa, which is the *mycobacterium* most closely related to Map and capable of infecting animals. The rational for this approach was that comparison of the proteomes of the two organisms would identify subspecies-specific proteins, including the products of differential gene regulation that would not be detected by a comparative genomics approach. In order to perform a comparison of IS901+ Maa and Map, it was necessary first to undertake significant development work to optimise and standardise the experimental and analytical procedures required. The standardized methods are detailed above. Since the proteome changes during the growth cycle, comparisons were made also between the proteomes obtained from the organisms at different stages in the growth cycle (both log and stationary phases were investigated).

On comparison of the proteomes, proteins that appeared to be uniquely expressed or upregulated in Map were picked from the gels and subjected to further investigation by MALDI-TOF analyses. It was possible to characterise 32 of these Map proteins and define the corresponding genes following MALDI-TOF and Mascot analyses. The proteomes were compared from different strains of the organisms to ensure that the proteins identified were representative of the subspecies. Comparison with the in vivo proteome of Map confirmed that the proteins were expressed during natural infection of the target species. An example of a Map proteome and a summary of the proteomic data is given in Table 1, which identifies proteins that are specific for Map and potentially suitable antigens for use in the present invention.

The genes encoding the Map-specific proteins were amplified by PCR and 30 of the Map-specific proteins were cloned into the pMAL-c2X vector (New England Biolabs Inc.) and expressed as fusion proteins with MBP. Purified recombinant proteins were prepared for use in immunological assays using the procedures described above.

Example 2

Recognition of the Map-Specific Proteins by the Cell-Mediated Immune Response of Infected Sheep To determine whether any of the Map-specific proteins would be suitable for use in a cell-mediated immunity assay, it was crucial to determine if they were recognized by the cell-mediated immune response of Map-infected animals. In order to undertake these experiments, it was necessary to identify subclinically infected sheep that were mounting a cell-mediated response to Map. To identify such animals, 35 sheep from a known infected flock were screened using the whole blood Bovigam IFN-γ assay using PPDJ (from Map), PPDA (from Maa) and PPDB (from *Mycobecterium bovis*) as the stimulatory antigens. Concavalin A (ConA) was included as a mitogen control to assess the health status of the cells. Nine animals were identified as having a significant positive response to PPDJ and were selected for further investigation. Control animals were taken from a flock with no history of paratuberculosis and tested in the IFN-γ assay using PPDJ and PPDA for a negative response. Sera from control animals were sent to BioBest Laboratories Ltd. (Pentlands Science Park, Penicuik, Scotland) for testing by ELISA to ensure that the animals did not have circulating antibodies to Map indicative of clinical infection. Faecal smears from the control animals were stained by Ziehl Nielsen staining as a final check to ensure that they were not infected with Map.

Figure 1:
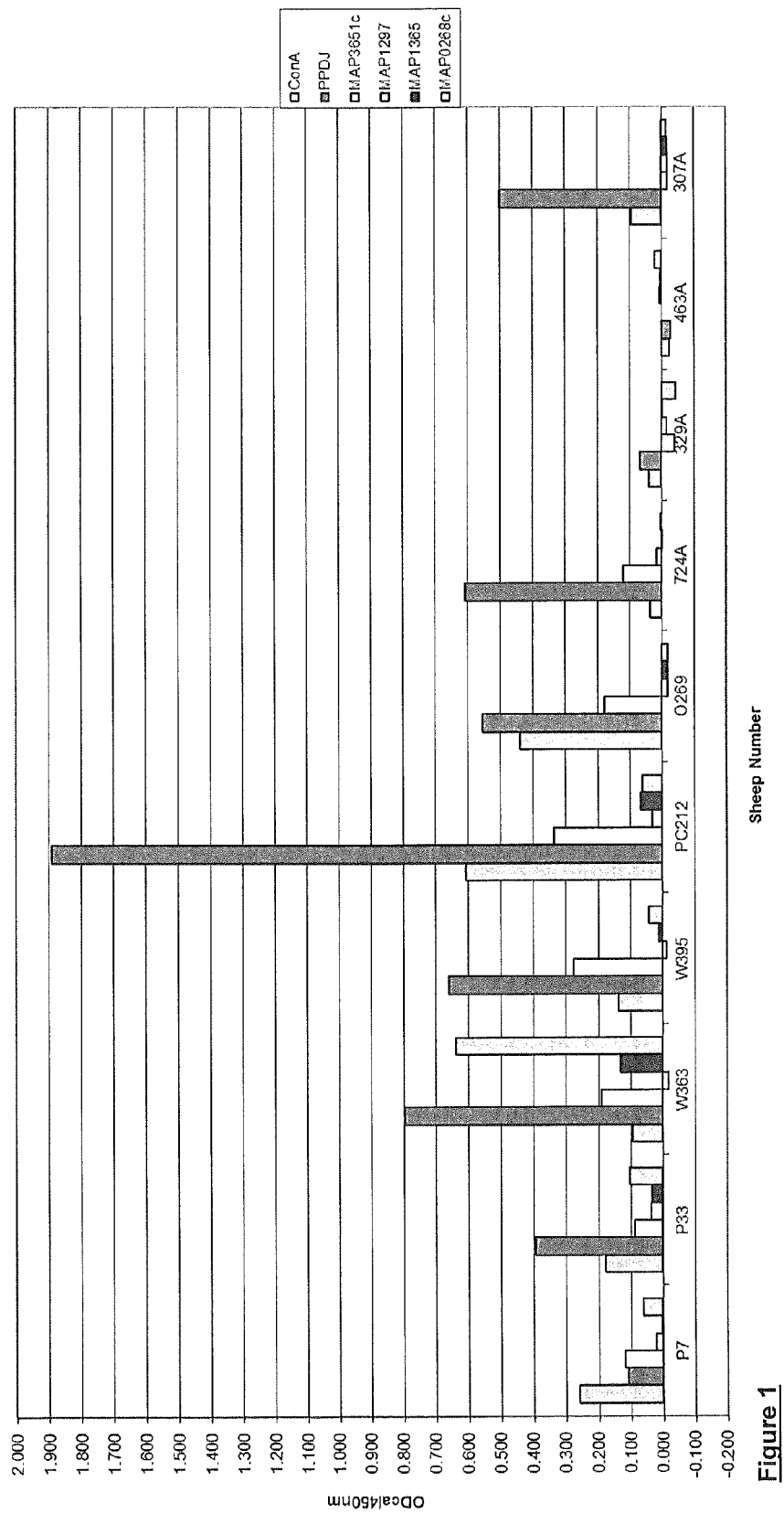
FIG. 1 shows the results of a IFN-γ ELISA showing cell-mediated immune responses to the Map-specific proteins of individual sub-clinical Map infected sheep (P7, P33, W363, W395, PC212, 0269) in comparison to control animals (724A, 329A, 463A, 307A)
Figure 2:
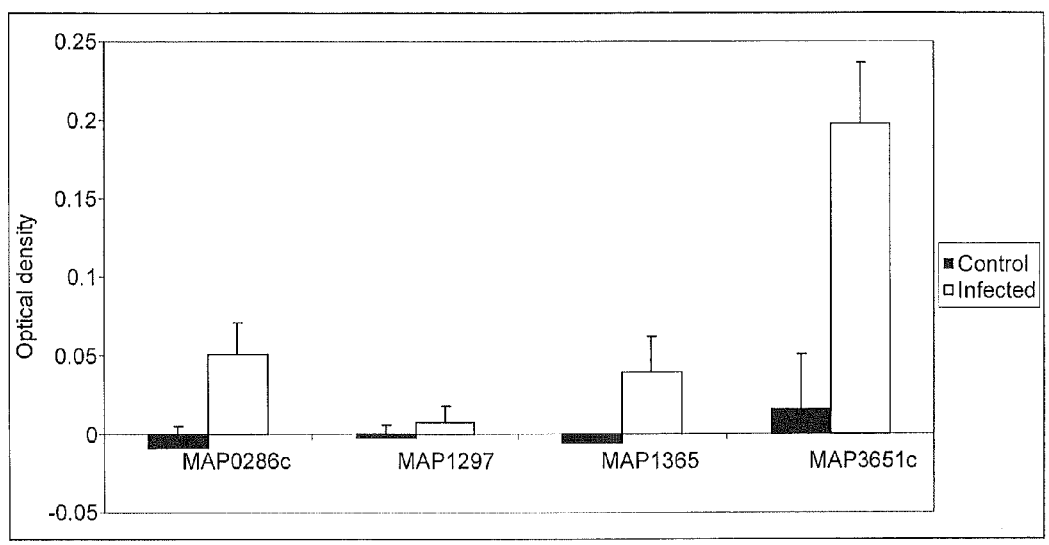
FIG. 2 shows a plot of the data in FIG. 1 showing the relative differences between the cell-mediated immune responses to the Map-specific proteins in the infected and control groups with raw means and standard errors.

Blood was taken from the animals and peripheral blood lymphocytes purified following hypotonic lysis and lymphoprep separation (as described above). The IFN-γ assay was performed using 30 recombinant Map-specific proteins, MBP, PPD-J, ConA and medium. OD values were corrected for both medium background and MBP for Map-specific proteins. Taking a cut-off value of a corrected OD >0.1 and a positive result in 2 or more of the subclinically infected sheep, 10 of the 30 recombinant Map-specific proteins appeared to elicit a cell-mediated response. Four of these proteins (MAP3651c, MAP1297, MAP1365 and MAP0268c) were recognised by 50% or more of the animals in the IFN-γ assay and are potential reagents for a cell-mediated immunity test for Map. The experiment was repeated with these four Map-specific proteins using blood from 6 subclinically infected and four control animals. Data from the Bovigam assay carried out in triplicate using these four proteins are given in FIG. 1 and following statistical analysis in FIG. 2. The means of the triplicates were used in subsequent analyses. FIG. 1 shows the results of the IFN-γ ELISA showing cell-mediated immune responses to the Map-specific proteins of the individual subclinical Map infected sheep (P7, P33, W363, W395, PC212, 0269) in comparison to control animals (724A, 329A, 463A, 307A). Box plots were drawn to compare the difference in variability of cell-mediated immune responses to the Map-specific proteins between the groups of infected animals (proteins preceded by I) and the control animals (proteins preceded by C). There was some evidence of a difference in variability between the groups and a clear outlier (observation 20, the value for 0268c for animal W363 in the infected group). The OD value was an order of magnitude higher than the other comparable values and this data point was removed from subsequent analyses. As this was the highest value for an infected animal it would not bias the results in favour of the infected group. FIG. 2 shows a plot of the data showing the relative differences between the cell-mediated immune responses to the Map-specific proteins in the infected and control groups with raw means and standard errors. Due to variability, the adjusted data (means of triplicates) were analysed using a linear mixed model, with group (control/infected) and protein fitted as categorical fixed effects and animal as a random effect. Ranks of the triplicate means (rather than the raw means) were computed and used in the statistical model. There was evidence of a group×protein interaction (P=0.025) which indicated that there were genuine differences between the control and infected groups for some of the proteins. For all proteins mean levels were higher in the infected group and the differences were markedly different for MAP0268c, MAP1365 and MAP3651c. This supports the raw data plotted in FIG. 2 and a two sample t-test confirmed MAP0268c and MAP3651c to be significant at the 5% significance level. The P value for MAP1365 is just short of statistical significance (P=0.1)

Whilst the present invention is particularly directed to the diagnosis of Map infection in sheep and cattle, the methods of the invention extend to detection of Map infection in any other susceptible animal species including, for example, deer, goats, badger, buffalo, bison, possums, pigs, camels and even man.

Example 3

Enhanced Stimulation of Cytokine Production in Ovine Blood with Cocktails of Map-Specific Antigens The sensitivity of immunoassays can often be increased by using a cocktail of antigens. In a small pilot experiment, the cell-mediated immune responses of two sheep subclinically infected with Map were measured in response to single antigen preparations and a cocktail of recombinant Map-specific proteins MAP3651c and MAP1365 as described above. The results are shown in FIG. 7. A combination of two Map-specific antigens stimulated an enhanced response in the Bovigam IFN-γ ELISA compared with the single antigen preparations although the magnitude of the response varied between sheep. Different combinations of the Map-specific recombinant antigens will need to be evaluated to determine the optimum mix for diagnostic assays.

Example 4

Recognition of the Map-Specific Proteins by the Cell-Mediated Response of Experimentally Infected Calves To determine if the Map-specific proteins were recognized by the cell-mediated immune response of another host species a calf model of infection was utilised. Calves were experimentally infected with Map and Maa as described above. Blood was collected, stimulated with preparations of the recombinant antigens and the cell-mediated responses measured using the Bovigam IFN-γ assay as described above. The results showed that the Map infected calves mounted a detectable cell-mediated immune response to all of the antigens compared with the uninfected control calves (FIG. 8).

The specificity of the cell-mediated immune response of Map-infected calves compared with Maa-infected calves to recombinant 3651c was evaluated. Blood was analysed from the two calves infected with $10^9$ Map and the 6 calves infected with $10^9$ Maa 48 and 54 weeks post infection, respectively, using the Bovigam IFN-γ ELISA as described above. Blood was stimulated with recombinant MAP3651c, PPDA and PPDJ. The results are shown in FIG. 9. There was a greater cell-mediated response to 3651c in the Map-infected calves than the Maa-infected calves although the magnitude of the response varied between the animals. These results show that MAP3651c can be used to differentiate between Map and Maa-infected animals.

TABLE 1

*Mycobacterium avium* subsp. *paratuberculosis* Specific Proteins, 2-D Analysis and Mass Spectrometry Data

| | | | 2-D Expression Analysis | | | Mass Spectrometry Identification | | | | |
|---|---|---|---|---|---|---|---|---|---|---|
| Annotation | Protein | Nominal Mass | Median Spot Vol | Percentage Increase in Expression | P Values Mann-Whitney | Mascot Score | PI | Peptide Count | Masses Searched | Sequence Coverage |
| MAP0068 | SsB | 17.5 | 0.51 | 99 | 0.002 | 149 | 5.12 | 11 | 28 | 66 |
| MAP0139c | | 23.6 | 0.05 | 100 | 0.002 | 56 | 9.95 | 10 | 107 | 54 |
| MAP0268c | | 23.8 | 0.26 | 100 | 0.002 | 106 | 4.96 | 7 | 16 | 39 |
| MAP0334 | | 34.5 | 0.09 | 100 | 0.002 | 147 | 5.34 | 10 | 17 | 33 |
| MAP0494* | | 38.5 | 0.36 | 89 | 0.002 | 180 | 5.85 | 11 | 16 | 47 |
| MAP1012c | | 37.5 | 0.07 | 100 | 0.003 | 118 | 4.6 | 13 | 57 | 48 |

TABLE 1-continued

Mycobacterium avium subsp. paratuberculosis Specific Proteins, 2-D Analysis and Mass Spectrometry Data

| | | | 2-D Expression Analysis | | | Mass Spectrometry Identification | | | | |
|---|---|---|---|---|---|---|---|---|---|---|
| Annotation | Protein | Nominal Mass | Median Spot Vol | Percentage Increase in Expression | P Values Mann-Whitney | Mascot Score | PI | Peptide Count | Masses Searched | Sequence Coverage |
| MAP1160c | | 29.4 | 0.38 | 58 | NS | 84 | 5.44 | 7 | 27 | 33 |
| MAP1293 | HisD | 49.4 | 0.04 | 89 | 0.002 | 94 | 4.92 | 12 | 33 | 27 |
| MAP1297 | HisA | 25.4 | 0.09 | 100 | 0.002 | 106 | 4.73 | 8 | 29 | 58 |
| MAP1365 | ArgF | 33.6 | 0.04 | 100 | 0.002 | 71 | 4.9 | 6 | 26 | 30 |
| MAP1564c | | 23.1 | 0.12 | 100 | NS | 110 | 5.66 | 8 | 23 | 43 |
| MAP1754c | Usp | 30.8 | 0.03 | 100 | 0.002 | 131 | 5.72 | 10 | 24 | 38 |
| MAP2541c | MDH | 34.5 | 0.09 | 100 | 0.002 | 208 | 4.87 | 13 | 18 | 44 |
| MAP2685 | | 21.3 | 0.20 | 39 | NS | 130 | 4.84 | 7 | 11 | 57 |
| MAP2872c | FabG5_2 | 26.7 | 0.37 | 75 | NS | 86 | 5.65 | 10 | 71 | 40 |
| MAP2878c | DapB | 25.6 | 0.38 | 58 | NS | 89 | 5.52 | 7 | 27 | 39 |
| MAP3175c | PrfB | 41.5 | 0.07 | 100 | 0.003 | 68 | 4.73 | 8 | 57 | 28 |
| MAP3205 | NuOE | 26.9 | 0.11 | 39 | NS | 66 | 4.66 | 6 | 31 | 31 |
| MAP3385 | | 32.3 | 0.11 | 39 | NS | 57 | 4.62 | 5 | 18 | 24 |
| MAP3457 | MetC | 47.6 | 0.07 | 68 | NS | 153 | 5.25 | 12 | 28 | 46 |
| MAP3491 | | 28.2 | 0.05 | 100 | NS | 124 | 5.45 | 8 | 17 | 49 |
| MAP3540c | | 25.1 | 0.03 | 100 | 0.002 | 124 | 5.18 | 9 | 23 | 38 |
| MAP3567 | | 30.1 | 0.40 | 88 | 0.002 | 217 | 5.7 | 14 | 33 | 66 |
| MAP3627 | | 23.1 | 0.18 | 100 | 0.002 | 92 | 5.4 | 7 | 22 | 34 |
| MAP3651c | FadE3_2 | 43.9 | 0.47 | 93 | 0.002 | 273 | 6.15 | 19 | 29 | 49 |
| MAP3692c | FabG4 | 47.1 | 0.14 | 23 | NS | 102 | 5.79 | 8 | 19 | 30 |
| MAP3693* | FadA2 | 46.7 | 0.11 | 73 | NS | 165 | 6.21 | 14 | 31 | 42 |
| MAP3841 | GrpE | 23.7 | 0.23 | 71 | NS | 151 | 4.58 | 11 | 24 | 42 |
| MAP3857 | UmpA | 18.7 | 0.06 | 100 | 0.002 | 103 | 6.06 | 7 | 19 | 49 |
| MAP3932c | MoA3 | 41.4 | 0.04 | 89 | 0.002 | 56 | 5.01 | 6 | 28 | 24 |
| MAP4147 | | 42.2 | 0.07 | 100 | 0.003 | 125 | 4.73 | 15 | 57 | 49 |
| MAP 4233 | Rpo | | 0.07 | 100 | 0.003 | 125 | 4.73 | 15 | 57 | 49 |

*Clones containing the sequence of these proteins were unobtainable after three attempts to amplify or clone the sequence. Median Spot vol is that of the M. avium subsp. paratuberculosis population. Percentage increase in expression is the difference of the spot volume medians expressed as a proportion of the median spot volume recorded for M. avium subsp. paratuberculosis

REFERENCES

Bannantine, J. P., E. Baechler, Q. Zhang, L. Li, and V. Kapur. 2002. Genome scale comparison of *Mycobacterium avium* subsp. *paratuberculosis* with *Mycobacterium avium* subsp. *avium* reveals potential diagnostic sequences. J. Clin. Microbiol. 40: 1303-1310.

Bannantine J. P., J. K. Hansen, M. L. Paustian, A. Amonsin, L-L. Li, J. R. Stabel, and V. Kapur. 2004. Expression and Immunogenicity of Proteins Encoded by Sequences Specific to *Mycobacterium avium* subsp. *paratuberculosis*. J. Olin, Microbiol. 42: 106-114.

Benjamini, Y. and Y. Hochberg. 1995. Controlling the false discovery rate: a practical and powerful approach to multiple testing. J. Roy. Stat. Soc., Ser. B. 57: 289-300.

Hughes, V., J. P. Bannantine, S. Denham, S. Smith, A. Garcia-Sanchez, J. Sales, M. Paustian, K. McLean, K. Stevenson. 2008. Proteome-determined *Mycobacterium avium* paratuberculosis-specific proteins: Immunogenicity in ovine paratuberculosis. Clin. Vaccine Immunol. 15: 1824-1833.

Hughes, V., S. Smith, A. Garcia-Sanchez, Sales, J., and K. Stevenson. 2007. Proteomic comparison of *Mycobacterium avium* subspecies *paratuberculosis* grown in vitro and isolated from clinical cases of ovine paratuberculosis. Microbiol. 153: 196-205.

Li, L., J. P. Bannantine, Q. Zhang, A. Amonsin, B. J., May, D. Alt, N. Banerji, S. Kanjilal and V. Kapur. 2005. The complete genome sequence of *M. avium* subsp. *paratuberculosis*. Proc. Natl. Acad. Sci. USA. 102 12344-12349.

Morrissey, J. H. 1981. Silver stain for proteins in polyacrylamide gels-a modified procedure with enhanced uniform sensitivity. Annal. Biochem. 117: 307-310.

Neuhoff, V., R. Stamm, and H. Eibl. 1985. Clear background and highly sensitive protein staining with coomassie blue dyes in polyacrylamide gels: a systematic analysis. Electrophoresis 6:427-448.

Perkins, D. N., D. J. Pappin, D. M. Creasy, and J. S. Cottrell. 1999. Probability-based protein identification by searching sequence data bases using mass spectrometry data. Electrophoresis. 20: 3551-3567.

The invention claimed is:

1. A method of detecting a cell-mediated immune response to one or more purified antigens of *Mycobacterium avium* subspecies *paratuberculosis* (Map) in an animal, the method comprising the step of:
   detection of a cell-mediated immune response by measuring the extent of lymphocyte activation and/or proliferation in response to said one or more purified antigens of Map,
   wherein the Map antigens are selected from the group consisting of MAP0268c; MAP1297; MAP1365 and MAP3651c.

2. The method of claim 1, wherein the cell-mediated immune response is measured by detecting a level of cytokine such as interferon gamma (IFN-γ), tumour necrosis factor alpha (TNF-α), transforming growth factor beta (TGF-β), interleukins IL-6, IL-10, IL-12, IL-17) and granulocyte-macrophage colony-stimulating factor (GM-CSF) using antibodies or indirectly from mRNA by RT-PCR or microarray.

3. The method of claim 1, wherein the method is carried out on a blood sample or fraction thereof, isolated from a subject, or a skin test such as a delayed hypersensitivity skin test.

4. The method of claim 3 wherein the sample of blood or fraction thereof is incubated with said one or more purified Map antigens, to allow any cell-mediated response to develop.

5. The method of claim 1 wherein the antigens are proteins, or fragments thereof, that are expressed by Map and elicit a detectable immune response in animals infected by Map greater than that elicited by the antigens of other closely related subspecies of *Mycobacterium avium* (*Mycobacterium avium* subspecies *avium* and *Mycobacterium avium* subspecies *silvaticum*).

6. The method of claim 1, wherein the antigens display little or no cross-reactivity with other related species, such as other subspecies of *Mycobacterium avium*, *Mycobacterium bovis* and/or *Mycobacterium tuberculosis*.

7. The method of claim 1, wherein the method uses two or more Map-specific antigens.

8. A kit for carrying out a method of diagnosing a Map infection comprising:
   one or more purified Map-specific proteins, or immunogenic fragments thereof, capable of eliciting a cell-mediated immune response; and
   an additional reagent or reagents for use in the method of diagnosis,
   wherein the one or more purified Map-specific proteins is selected from the group consisting of MAP0268c; MAP1297; MAP1365; and MAP3615c, and wherein the additional reagent or reagents for use in the method of diagnosis is for detection of the cell-mediated immune response by measuring the extent of lymphocyte activation and/or proliferation in response to the one or more purified Map-specific proteins.

9. The kit of claim 8, wherein the cell-mediated immune response to the one or more purified Map-specific proteins is measured by detecting a level of a cytokine using an anti-cytokine antibody or antibodies, or indirectly from mRNA by RT-PCR or microarray.

10. The kit of claim 8, wherein the additional reagent or reagents comprises an anti-IFN-γ antibody.

* * * * *

UNITED STATES PATENT AND TRADEMARK OFFICE
CERTIFICATE OF CORRECTION

| | |
|---|---|
| PATENT NO. | : 9,005,908 B2 |
| APPLICATION NO. | : 12/994876 |
| DATED | : April 14, 2015 |
| INVENTOR(S) | : Stevenson et al. |

It is certified that error appears in the above-identified patent and that said Letters Patent is hereby corrected as shown below:

In the Specification:
Column 8, Lines 27 and 28: Please begin a new paragraph after "Lymphocytes" so that it reads as follows -- Preparation and Stimulation of Ovine Peripheral Blood Lymphocytes 20 ml of blood were collected by venipuncture and --

Columns 11 and 12, Table 1: Please correct the Table headers below

"T"

| *Mycobacterium avium* subsp. *paratuberculosis* Specific Proteins, 2-D Analysis and Mass Spectrometry Data | | | | | | | | | | |
|---|---|---|---|---|---|---|---|---|---|---|
| | | | 2-D Expression Analysis | | | | Mass Spectrometry Identification | | | |
| Annotation | Protein | Nominal Mass | Median Spot Vol | Percentage Increase in Expression | P Values Mann-Whitney | Mascot Score | PI | Peptide Count | Masses Searched | Sequence Coverage | to read

| *Mycobacterium avium* subsp. *paratuberculosis* Specific Proteins, 2-D Analysis and Mass Spectrometry Data | | | | | | | | | | |
|---|---|---|---|---|---|---|---|---|---|---|
| | | | 2-D Expression Analysis | | | Mass Spectrometry Identification | | | | |
| Annotation | Protein | Nominal Mass | Median Spot Vol | Percentage Increase in Expression | P Values Mann-Whitney | Mascot Score | PI | Peptide Count | Masses Searched | Sequence Coverage |

--

Signed and Sealed this
Twenty-ninth Day of December, 2015

Michelle K. Lee
*Director of the United States Patent and Trademark Office*

CERTIFICATE OF CORRECTION (continued)
U.S. Pat. No. 9,005,908 B2

In the Specification:
Columns 13 and 14: TABLE 1 – continued: Please correct the table headers below "
| *Mycobacterium avium* subsp. *paratuberculosis* Specific Proteins, 2-D Analysis and Mass Spectrometry Data | | | | | | | | | | |
|---|---|---|---|---|---|---|---|---|---|---|
| | | | 2-D Expression Analysis | | | Mass Spectrometry Identification | | | | |
| Annotation | Protein | Nom-inal Mass | Median Spot Vol | Percentage Increase in Expression | P Values Mann-Whitney | Mascot Score | PI | Peptide Count | Masses Searched | Sequence Coverage |

"

to read

| *Mycobacterium avium* subsp. *paratuberculosis* Specific Proteins, 2-D Analysis and Mass Spectrometry Data | | | | | | | | | | |
|---|---|---|---|---|---|---|---|---|---|---|
| | | | 2-D Expression Analysis | | | Mass Spectrometry Identification | | | | |
| Annotation | Protein | Nominal Mass | Median Spot Vol | Percentage Increase in Expression | P Values Mann-Whitney | Mascot Score | PI | Peptide Count | Masses Searched | Sequence Coverage |

--

In the Claims:
Column 21, Claim 2, Line 36:
Please correct "interleukins IL-6,"
      to read -- interleukins (IL-2, IL-6, --